US008415300B2

(12) United States Patent
Deghenghi et al.

(10) Patent No.: US 8,415,300 B2
(45) Date of Patent: *Apr. 9, 2013

(54) SUSTAINED RELEASE OF MICROCRYSTALLINE PEPTIDE SUSPENSIONS

(75) Inventors: Romano Deghenghi, St. Cergue (CH); Francois Boutignon, Ermont (FR)

(73) Assignee: Medical Research Council Technology, London (GB)

( * ) Notice: Subject to any disclaimer, the term of this patent is extended or adjusted under 35 U.S.C. 154(b) by 0 days.

This patent is subject to a terminal disclaimer.

(21) Appl. No.: 13/224,105

(22) Filed: Sep. 1, 2011

(65) Prior Publication Data

US 2011/0312889 A1 Dec. 22, 2011

Related U.S. Application Data

(63) Continuation of application No. 12/795,246, filed on Jun. 7, 2010, now abandoned, which is a continuation of application No. 11/450,292, filed on Jun. 12, 2006, now abandoned, which is a continuation of application No. 10/080,130, filed on Feb. 19, 2002, now Pat. No. 7,098,305.

(60) Provisional application No. 60/317,616, filed on Sep. 6, 2001.

(51) Int. Cl.
*A61K 38/09* (2006.01)
*A61K 38/00* (2006.01)
*A61K 38/08* (2006.01)
*A61P 43/00* (2006.01)
*C07K 2/00* (2006.01)
*C07K 7/06* (2006.01)

(52) U.S. Cl. ....... 514/10.4; 514/1.1; 514/10.3; 530/300; 530/326; 530/328; 530/345

(58) Field of Classification Search .................. None
See application file for complete search history.

(56) References Cited

U.S. PATENT DOCUMENTS

| | | | | |
|---|---|---|---|---|
| 2,668,866 | A | 2/1954 | Good et al. | 260/683.5 |
| 4,139,494 | A | 2/1979 | Itoh et al. | 252/455 R |
| 4,186,078 | A | 1/1980 | Itoh et al. | 208/27 |
| 4,239,546 | A | 12/1980 | Russell et al. | 106/270 |
| 4,256,737 | A | 3/1981 | Nestor et al. | 424/177 |
| 4,415,649 | A | 11/1983 | Munger et al. | 430/271 |
| 4,839,422 | A | 6/1989 | McElrath et al. | 525/74 |
| 5,110,904 | A | 5/1992 | Haviv et al. | 530/313 |
| 5,648,096 | A | 7/1997 | Gander et al. | 424/489 |
| 5,773,032 | A | 6/1998 | Engel et al. | 424/501 |
| 6,258,933 | B1 | 7/2001 | Günther et al. | 530/344 |
| 7,098,305 | B2 | 8/2006 | Deghenghi et al. | 530/326 |
| 2002/0198146 | A1 | 12/2002 | Damm et al. | 514/12 |
| 2006/0228385 | A1 | 10/2006 | Deghenghi et al. | 424/400 |

FOREIGN PATENT DOCUMENTS

| | | |
|---|---|---|
| DE | 26 44 519 | 4/1977 |
| GB | 1 245 187 | 9/1971 |
| GB | 2 052 258 | 1/1981 |
| JP | 3-101695 | 4/1991 |
| JP | 4-505750 | 10/1992 |
| JP | 8-504209 | 5/1996 |
| JP | 8-505611 | 6/1996 |
| WO | WO 89/07450 | 8/1989 |
| WO | WO 92/19651 | 11/1992 |
| WO | WO 94/13313 | 6/1994 |
| WO | WO 94/14841 | 7/1994 |
| WO | WO 95/15767 | 6/1995 |
| WO | WO 98/25642 | 6/1998 |
| WO | WO 00/47234 | 8/2000 |

OTHER PUBLICATIONS

Definition of analog from http://cancerweb.ncl.ac.uk/omd/about.html, pp. 1-5. Accessed Jul. 7, 2005.*
Berendsen H. J.C., "A Glimpse of the Holy Grail?", Science, vol. 282, pp. 642-643 (1998.
Deghenghi, R., "Antarelix in Treatment With GnRH Analogues: Controversies and Perspectives", M. Filicori and C. Flamigni, Eds., The Parthenon Publishing Group, pp. 89-91, (1996).
Deghenghi, R. et al., "Antarelix (EP 24332) a Novel Water Soluble LHRH Antagonist", Biomed. & Pharmacother., vol. 47 pp. 107-110 (1993).
Martindale, M.F., "The Complete Drug Reference", Insulin, K. Parfitt, ed., 32nd ed., pp. 322-330 (1999).
Powell et al., "Parenteral Peptide Formulations: Chemical and Physical Properties of Native Luteinizing Hormone-Releasing Hormone (LHRH) and Hydrophobic Analogues in Aqueous Solution", Pharm. Res., vol. 8, No. 10, pp. 1258-1263 (1999).
Rivier, J., "GnRH Analogues Towards the Next Millennium", B. Lunenfield, Ed., The Parthenon Publishing Group, New York, London, pp. 31-45, (1999).
Rudinger, J., "Characteristics of the Amino Acids as Components of a Peptide Hormone Sequence", Peptide Hormones, Edited by J.A. Parsons, University Park Press, (1976).
Sigma, "Designing Custom Peptides", Accessed Dec. 16, 2004.
Schnitzel R. et al., "The Phosphate Recognition Site of *Escherichia coli* Maltodextrin Phosphorylase, FEBS", vol. 286, Nos. 1,2, pp. 125-128 (1991).
Voet D. et al., Biochemistry, Second Edition, John Wiley & Sons, Inc., pp. 235-241 (1995).

(Continued)

Primary Examiner — Julie Ha
(74) Attorney, Agent, or Firm — Winston & Strawn LLP

(57) ABSTRACT

A fluid, milky microcrystalline aqueous suspension of a peptide or peptidomimetic and a counter-ion of a strong proton donor in water, wherein the peptide or peptidomimetic and counter-ion are present in amounts and at a molar ratio sufficient to form the suspension upon mixing and without formation of a gel. Also, lyophilized compositions that include a dried suspension, methods of making the lyophilized composition, methods of preparing the suspension, and sustained release formulations prepared by the methods.

21 Claims, 1 Drawing Sheet

OTHER PUBLICATIONS

Samant M. P., et al., Iterative Approach to the Discovery of Novel Degarelix Analogues: Substitutions at Positions 3, 7, and 8. Part II, *J. Med. Chem.*, 48(15), pp. 4851-4860 (2005).

Ljungqvist A., et al.,"Antide and Related Antagonists of Luteinizing Hormone Release With Long Action and Oral Activity", *Proc. Natl. Acad. Sci.*, 85, 1pp. 8236-8240 (1988).

Jiang G.., et al., GnRH Antagonists: A New Generation of Long Acting Analogues Incorporating p-Ureido-phenylalanines At Positions 5 and 6, *J. Med. Chem.*, 44(3), pp. 453-467 (2001).

Ngo JT, Marks J, Karplus M, "Computational Complexity, Protein Structure Prediction, and the Levinthal Paradox," The Protein Folding Problem and Tertiary Structure Prediction, K. Merc Jr. and S. Le Grand Edition, 1994, pp. 491-495.

Bradley CM, Barrick D, "Limits of Cooperativity in a Structurally Modular Protein: Response of the Notch Ankyrin Domain to Analogous Alanine Substitutions in Each Repeat," J. Mol. Biol., 2002, 324: 373-386.

Non-Final Office Action dated Dec. 19, 2005 for, U.S. Appl. No. 10/080,130.
Non-Final Office Action dated Sep. 1, 2004 for, U.S. Appl. No. 10/080,130.
Non-Final Office Action dated Jul. 9, 2008 for, U.S. Appl. No. 11/450,292.
Final Office Action dated Apr. 16, 2009 for U.S. Appl. No. 11/450,292.
Final Office Action dated Dec. 8, 2009 for U.S. Appl. No. 11/450,292.
Non-Final Office Action dated Jul. 9, 2008 for, U.S. Appl. No. 11/450,293.
Final Office Action dated Mar. 10, 2009 for U.S. Appl. No. 11/450,293.
Final Office Action dated Mar. 1, 2011 for U.S. Appl. No. 12/795,246.

* cited by examiner

TEVERELIX-TFA 65mg/ml in 5% mannitol
1mg/ rat : pharmacodynamic

TEVERELIX-TFA 65mg/ml in 5% mannitol
1mg/ rat : pharmacokinetic

SUSTAINED RELEASE OF MICROCRYSTALLINE PEPTIDE SUSPENSIONS

CROSS-REFERENCE TO RELATED APPLICATIONS

This application is a continuation of U.S. application Ser. No. 12/795,246 filed Jun. 7, 2010 now abandoned which is a continuation of U.S. application Ser. No. 11/450,292 filed Jun. 12, 2006 (now abandoned) which is a continuation of U.S. application Ser. No. 10/080,130 filed Feb. 19, 2002 (now U.S. Pat. No. 7,098,305) which claims the benefit of U.S. Provisional Application No. 60/317,616 filed Sep. 6, 2001, the entire disclosure of each of which is incorporated herein by reference.

BACKGROUND OF THE INVENTION

There is frequently a need to deliver biologically active peptides to animals and humans in formulations providing a sustained release of the active principle. Such formulations may be provided by incorporating the active principle in biodegradable and biocompatible polymers in the form of microcapsules, microgranules or implantable rods, or alternatively using mechanical devices such as micropumps or non-biodegradable containers. If the peptide is highly soluble in aqueous media, it can be formulated as a complex with non-degradable polymers such as cellulose derivatives, or mixed with polymer solutions, which form a gel upon parenteral injection, from which the active peptide is slowly released.

All the above-mentioned formulations have drawbacks, and limitations, such as the large volume of suspending fluids or the need to remove the non-degradable device. In the case of gel forming peptides, there is frequently a problem of bioavailability, which interferes with the desired sustained action of the active principle.

Some of the problems due to physico-chemical aspects of peptides have been described in an article by R. Deghenghi "Antarelix" in Treatment with GnRH Analogs: Controversies and Perspectives", edited by M. Filicori and C. Flamigni, The Parthenon Publishing Group, New York and London 1996, pages 89-91. Additional problems were illustrated by J. Rivier "GnRH analogues towards the next millennium" in GnRH Analogues, edited by B. Lunenfeld, The Parthenon Publishing Group, New York and London 1999, pages 31-45 and by other workers such as M. F. Powell et al. "Parenteral Peptide Formulations: Chemical and Physical Properties of Native LHRH and Hydrophobic Analogues in Aqueous Solution" in Pharmaceutical Research, Vol. 8, 1258-1263 (1991).

Accordingly, there is a need for new formulations and methods of administration that avoid these problems, and this need is addressed by the present invention.

SUMMARY OF THE INVENTION

The present invention relates to a fluid, milky microcrystalline aqueous suspension of a peptide or peptidomimetic and a counter-ion of a strong proton donor in water. The peptide or peptidomimetic and counter-ion are present in amounts and at a molar ratio sufficient to form the suspension of the peptide or peptidomimetic upon mixing without formation of a gel.

In one embodiment, the counter-ion is trifluoromethanesulfonic acid, benzenesulfonic acid, trifluoroacetic acid, or sulfuric acid. Generally, the counter-ion is a strong acid and the peptide is a GnRH analogue. The GnRH analogue is preferably a GnRH antagonist.

In another embodiment, the GnRH antagonist is Ac-D-Nal-D-Cpa-D-Pal-Ser-Tyr-D-Hci-Leu-Ilys-Pro-D-Ala-NH$_2$. In yet another embodiment, the GnRH antagonist is Azaline B, Abarelix, Antide, Ganirelix, Cetrorelix, or FE200486 and is in the form of an alkylsulfonate, arylsulfonate, trifluoroacetate or sulfate salt.

The peptide may also be a somatostatin analogue. The somatostatin analogue may be, for example, Vapreotide, Octreotide, Lanreotide or SOM 230.

Generally, the peptide or peptidomimetic forms a salt with the counter-ion, and the salt is suspended in the aqueous medium at a concentration of equal to or higher than 25 mg/mL. The aqueous suspension usually contains an isotonic agent, such as mannitol.

Typically, the suspension also includes a pharmaceutically acceptable excipient. The amount of peptide or peptidomimetic generally ranges from about 0.1 to 5 mg per kg body weight of a mammal or human to which the suspension is to be administered. The peptide is preferably at least partially in the form of microcrystals having a particle size of from about 1 μm to 150 μM.

The present invention also relates to a lyophilized composition that includes a dried suspension. In addition, the present invention, relates to a method of making the lyophilized composition by associating the peptide or peptidomimetic with a counter-ion of a strong proton donor in an amount and at a molar ratio that are sufficient to provide the suspension without formation of a gel, and lyophilizing the suspension to obtain the composition.

The present invention further relates to a method of preparing a fluid, milky microcrystalline aqueous suspension of a peptide or peptidomimetic that includes adding water or a buffer solution to the lyophilized composition with mixing to obtain the suspension.

A method of preparing a fluid, milky microcrystalline aqueous suspension of a peptide or peptidomimetic is also encompassed by the present invention. The method includes associating the peptide or peptidomimetic with the counter-ion in an amount and at a molar ratio with the peptide that are sufficient to provide the fluid, milky microcrystalline aqueous suspension without formation of a gel; lyophilizing the suspension to form a lyophilized composition; and adding water or a buffer solution to the lyophilized composition with mixing to obtain the suspension.

Furthermore, the present invention relates to a method of preparing a fluid, milky microcrystalline aqueous suspension of a peptide or peptidomimetic that includes associating the peptide or peptidomimetic with the counter-ion in an amount and at a molar ratio that are sufficient to provide the fluid, milky microcrystalline aqueous suspension without formation of a gel.

The suspension is generally prepared to provide a sustained release formulation of the peptide or peptidomimetic such that, when administered to a subject, the peptide or peptidomimetic is released in vivo over a period of at least two weeks. Preferably, the counter-ion is a trifluoromethanesulfonic acid, benzenesulfonic acid, trifluoroacetic acid or sulfuric acid. Typically, the counter-ion is a strong acid and the peptide is a GnRH analogue. The GnRH analogue is, for example, a GnRH antagonist. The GnRH antagonist is preferably Ac-D-Nal-DCpa-D-Pal-Ser-Tyr-D-Hci-Leu-Ilys-Pro-D-Ala-NH$_2$. The GnRH antagonist is typically Azaline B, Abarelix, Antide, Ganirelix, Cetrorelix, or FE200486 and is in the form of an alkylsulfonate, arylsulfonate, trifluoroacetate or sulfate salt.

The peptide is typically a somatostatin analogue. Preferably, the somatostatin analogue is Vapreotide, Octreotide, Lanreotide, or SOM 230. The peptide or peptidomimetic usually forms a salt with the counter-ion, and the salt is suspended in the aqueous medium at a concentration of at least 25 mg/mL.

In one embodiment, the aqueous suspension is injected parenterally into a mammal or human subject to obtain a sustained release of the peptide or peptidomimetic over at least one month. The amount of peptide or peptidomimetic in the suspension to be injected generally ranges from about 0.1 to 5 mg per kg body weight of the mammal or human subject.

A sustained release formulation of a peptide or peptidomimetic prepared by the method of the present invention, when administered to a subject, generally releases the peptide or peptidomimetic in vivo over a period of at least two weeks.

DETAILED DESCRIPTION OF THE PREFERRED EMBODIMENTS

Figure 1:
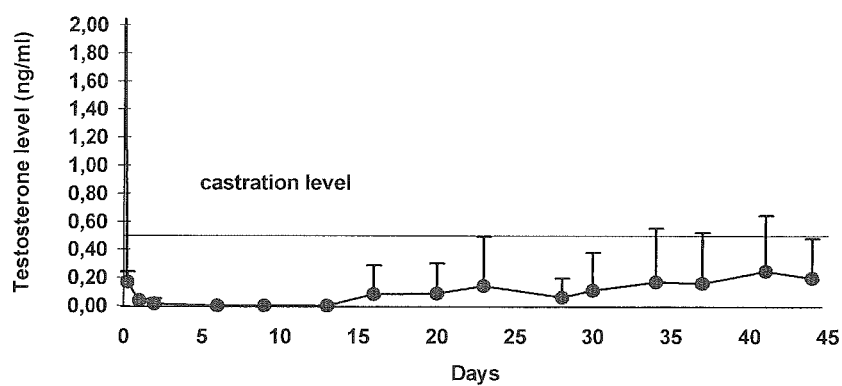
FIG. 1 is a graph which illustrates the pharmacodynamic effect (testosterone suppression) obtained by subcutaneous injection in rats of a suspension of Teverelix trifluoroacetate according to the invention.

The present invention is directed to the unexpected discovery that certain peptides can be prepared or associated with various counter-ions and simply formulated to provide desirable suspensions of the peptide, which suspensions are highly useful for administering the suspension by injection. In particular, a fluid, milky, stable microcrystalline suspension of the peptide is obtained without formation of a gel that would interfere with the handling of the suspension or the bioavailability of the peptide after injection.

The peptide that is to be utilized in the present suspension can be any one of a variety of well known bioactive peptides or peptide analogues which mimic such peptides. Advantageously, these peptides are formulated to obtain a delayed and sustained release of the peptide after injection. While any peptide can be utilized in this invention, those peptides or peptidomimetics having between 3 and 45 amino acids have been found to be the most suitable. In particular, representative peptides or peptidomimetics are well known to those of ordinary skill in the art and need not be exhaustively mentioned here. Typical examples include GnRH analogues and antagonists, as well as somatostatin and analogues thereof. Specific peptides include Azaline B, Abarelix, Antide, Ganirelix, Cetrorelix, FE 200486, Vapreotide, Octreotide, Lanreotide and SOM-230. These peptides have between 6 and 12 amino acids and are synthetically made to mimic the biological activity of GnRH or somatostatin. The examples mention further preferred peptides.

It has been found that certain counter-ions are highly preferred for obtaining sustained release of the peptide. Suitable counter-ions are those which are strong proton donors. While many compounds are well known to provide this function, the most preferred are strong acids. Sulfuric acid, a well known commodity, is quite useful for this purpose, as are other strong inorganic acids. Sulfuric is preferred due to its ready formation of suitable sulfate salts with the peptides of the invention. Strong organic acids can also be used as counter-ions. These acids include sulfonic acids, such as trifluoromethanesulfonic acid and benzene sulfonic acid. Others, such as trifluoroacetic acid or other fluorinated acids can be used if desired.

The amount of counter-ion is preferably that which is in excess of what is necessary to form a stoichiometric salt of the peptide. The amount of counter-ion is typically at least 1.6 mol acid/mole peptide and preferably 2 mol/mol or greater. While no upper limit has been determined, the amount can be as high as 10 mol/mol. In addition, the injectable suspension should be concentrated to obtained the most desirable release profiles. By concentrated, we mean that the amount of peptide should be above 2.5% by weight of the overall formulation. This is conveniently achieved by adding to water or a buffer solution at least 25 mg/mL of the peptide. Amounts of as high as 100 mg/mL can be used, and these suspensions can also contain other additives. In addition to conventional pharmaceutically acceptable excipients, an isotonic agent, such as mannitol, can be included for its known purpose. Other usual pharmaceutical additives can be included, as desired.

The suspensions can be dried by freeze-drying or spray drying to form lyophilized compositions that can be stored as is and later reconstituted with sterile water or buffer solutions when an injectable formulation is to be prepared. These lyophilized compositions can be stored for relatively long periods of time prior to use. Also they can be easily sterilized and handled until the time when they are to be reconstituted.

An additional advantage of this discovery is the small volume of such suspensions, allowing parenteral injections through a fine needle and thus improving the local tolerance of the injected material. Furthermore, the material can also be used for the local treatment of diseased tissues, e.g., brachytherapy. The peptide is partially or totally in the microcrystalline form having a particle size of between about 1 and 150 µm, and preferably between about 5 and 25 µm. These small particles easily pass through the injection needle. In such injections, the amount of peptide ranges from about 0.1 to 5 mg per kg body weight of the mammal or human to which the suspension is to be administered.

Figure 2:
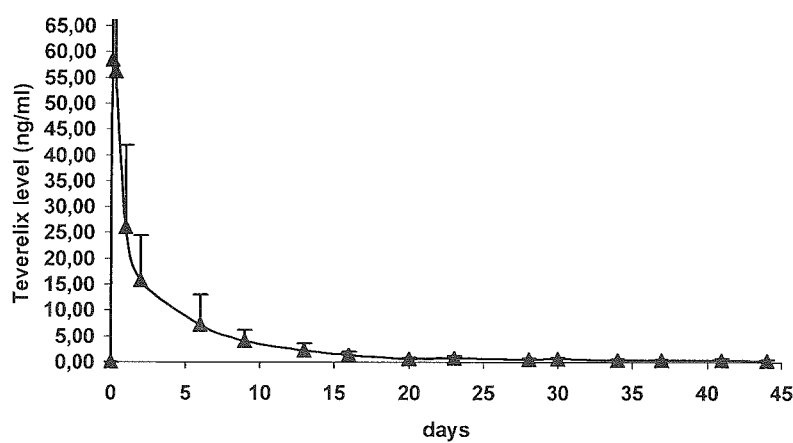
FIG. 2 is a graph which illustrates the sustained release of the peptide Teverelix for several weeks in rats injected with the suspension of Teverelix trifluoroacetate according to the invention.

A specific discovery was that a highly concentrated aqueous suspension of the peptide of the formula Ac-D-Nal-D-pClPhe-D-Pal-Ser-Tyr-D-Hci-Leu-Lys(iPr)-Pro-D-Ala-$NH_2$ (Teverelix, a GnRH antagonist) as a trifluoroacetate (TFA) or sulfate salt does not, as might be expected by its hydrophobic character, form a gel but instead forms a microcrystalline milky suspension which is easy to inject parenterally in animals or humans, and which releases the active principle over several weeks (see FIGS. 1 and 2). Such behavior is not elicited by other salts such as the acetate, which result in the expected, but unwanted, formation of gels with poor bioavailability in vivo.

The invention thus represents a simple and elegant solution to the problem of how to suppress gelation of peptide salts while obtaining a prolonged sustained delivery of peptides in the form of highly concentrated suspensions.

EXAMPLES

Example 1

200 µL of 5% mannitol were added to approximately 15 mg of the LHRH antagonist Teverelix trifluoroacetate. The mixture was stirred using vortex during one minute and a flowing milky pearly suspension was obtained. The suspension is made of microcrystals of about 10 µm length. Microcrystals may clump together to form urchin like structures. The suspension was injected in rats (1 mg) sub-cutaneously and provided the pharmacodynamic effect of testosterone suppression for more than 45 days (FIG. 1). The pharmacokinetic analysis showed a sustained release of the peptide for several weeks (FIG. 2).

Example 2

200 μL of water were added to approximately 15 mg of the LHRH antagonist Teverelix trifluoroacetate. The mixture was stirred using vortex during one minute and a flowing milky pearly suspension was obtained.

Example 3

200 μL of water were added to approximately 15 mg of the LHRH antagonist Teverelix acetate. The mixture was stirred using vortex during one minute and a transparent gel was obtained. The addition of 20 μL of TFA (3 mols/mol) to the gel resulted in the formation of a fluid, flowing milky pearly suspension.

Example 4

200 μL of 100 mM TFA were added to approximately 15 mg of the LHRH antagonist Teverelix acetate (2 mols/mol) to obtain a flowing milky suspension. In addition, mixing 200 μL of 75 mM TFA with approximately 15 mg of the LHRH antagonist Teverelix acetate (1.5 mol/mol) resulted in a transparent gel being obtained after mixing. In another study, 100 μL of TFA of various concentrations were added to 7.5 mg of the LHRH antagonist Teverelix acetate, with the TFA/Teverelix molar ratio ranging from 1 to 3. A flowing milky suspension was obtained with molar ratios of 1.6, whereas gels were obtained at other molar ratios.

Example 5

200 μL of 150 mM TFA were added to amounts of the LHRH antagonist Teverelix acetate ranging from 5 to 30 mg (concentration ranging from 25 to 150 mg/mL). A flowing milky suspension was obtained with concentrations up to 100 mg/mL.

Example 6

200 μL of 150 mM TFA were added to approximately 15 mg of the LHRH antagonist Teverelix acetate (3 mols/mol) and a flowing milky suspension was obtained after mixing. The suspension was freeze-dried overnight. 200 μL of water or 5% mannitol were added to the lyophilisate and a flowing milky suspension was obtained after mixing and reconstitution.

Example 7

1 mL of 150 mM TFA were added to approximately 75 mg of the LHRH antagonist Teverelix acetate (3 mols/mol) and a flowing milky suspension was obtained after mixing. The suspension was freeze-dried overnight. 1 mL of water and 0.2 M acetate buffer pH 4.0 were added to the lyophilisate and a flowing milky suspension was obtained after mixing and reconstitution. These suspensions were stable for at least 3 days at room temperature.

Example 8

100 μL of a 250 mM $H_2SO_4$ were added to 7.5 mg of the LHRH antagonist Teverelix acetate (5 mols/mol) and a flowing milky suspension was obtained after several hours. The suspension is made of microcrystals of about 100 μm length. Microcrystals may assemble together to form urchin like structures. The suspension was freeze-dried overnight. 100 μl of water or 5% mannitol were added to the lyophilisate and a flowing milky suspension was obtained after mixing and reconstitution.

Example 9

100 μL of a 150 mM trifluoromethane sulfonic acid solution were added to 7.5 mg of Teverelix acetate to obtain a free flowing milky suspension after mixing.

Example 10

100 μL of a 150 mM solution of benzenesulfonic acid were added to 7.5 mg Teverelix hydrochloride to give after a mixing a free flowing suspension.

Example 11

100 μL of a 200 mM solution of trifluoroacetic acid solution were added to 2.5 mg of Cetrorelix acetate to obtain a milky free flowing suspension.

Example 12

Free flowing suspensions were obtained by adding 100 μL of a 150 mM trifluoroacetic acid solution to 7.5 mg each of the following somatostatin analogues:
D-Phe-c[Cys-Tyr-D-Trp-Lys-Val-Cys]Trp-$NH_2$
D-2Me-Trp-c[Cys-Phe-D-Trp-Lys-Thr-Cys]-Trp(2Me)-$NH_2$
D-Nal-c[Cys-Tyr-D-Trp-Lys-Val-Cys]-Trp(2Me)-$NH_2$
D-Phe-c[Cys-Tyr-D-Trp-Lys-Val-Cys]-Trp(2Me)-$NH_2$

Example 13

100 μL of a 5% mannitol-water solution were added to approximately 5 mg of the somatostatin analog known under the designation SOM 230, i.e., ETD-carboxy-c[Hyp-Phg-D-Trp-Lys-Tyr(Bzl)-Phe], as the trifluoroacetate salt. A milky free flowing suspension was thus obtained.

What is claimed is:

1. A fluid, milky microcrystalline aqueous suspension comprising a hydrophobic peptide and trifluoroacetic acid, wherein the peptide is a GnRH antagonist selected from the group consisting of Azaline B, Abarelix, Antide, Ganirelix, Cetrorelix, FE200486, or Ac-D-Nal-D-Cpa-D-Pal-Ser-Tyr-D-Hci-Leu-Ilys-Pro-D-Ala-$NH_2$, and the peptide salt is present in amounts and at a molar ratio sufficient to form, upon mixing with water, the suspension without formation of a gel.

2. The suspension of claim 1 in which the GnRH antagonist is Ac-D-Nal-D-Cpa-D-Pal-Ser-Tyr-D-Hci-Leu-Ilys-Pro-D-Ala-$NH_2$ trifluoroacetate.

3. The suspension of claim 1 in which the hydrophobic peptide salt is suspended in the aqueous medium at a concentration of equal to or higher than 25 mg/ml.

4. The suspension of claim 1 in which the aqueous suspension contains an isotonic agent.

5. The suspension of claim 4 in which the isotonic agent is mannitol.

6. The suspension of claim 1 in which the aqueous suspension contains a pharmaceutically acceptable excipient.

7. The suspension of claim 1 wherein the microcrystals are in the form of needles having a particle size of between about 5 and 150 μm.

8. A lyophilized composition comprising the dried suspension of claim 1.

9. A method of preparing a lyophilized composition which comprises freeze-drying or spray-drying suspension according to claim 1 to obtain the composition.

10. A method of preparing an injectable fluid, milky, microcrystalline aqueous suspension of a hydrophobic peptide which comprises reconstituting with water or a buffer solution the lyophilized composition of claim 8.

11. A method of preparing a sustained release formulation of a hydrophobic peptide which comprises providing the peptide in the suspension of claim 1.

12. The method of claim 11 in which the GnRH antagonist is Ac-D-Nal-D-Cpa-D-Pal-Ser-Tyr-D-Hci-Leu-Ilys-Pro-D-Ala-NH$_2$ trifluoroacetate.

13. The method of claim 11 in which the hydrophobic peptide salt is suspended in the aqueous medium at a concentration of equal to or higher than 25 mg/ml.

14. The method of claim 11 in which the aqueous suspension contains an isotonic agent.

15. The method of claim 14 in which the isotonic agent is mannitol.

16. The method of claim 11 in which the aqueous suspension contains a pharmaceutically acceptable excipient.

17. The method of claim 11 in which the aqueous suspension is obtained extemporaneously from a lyophilized peptide salt.

18. A method of preventing gel formation while producing the aqueous suspension of claim 1, which comprises forming a salt by contacting the hydrophobic peptide with trifluoroacetic acid.

19. The suspension of claim 1 in which the peptide antagonist is Abarelix.

20. The suspension of claim 19 comprising the hydrophobic peptide salt is suspended in the aqueous medium at a concentration of equal to or higher than 25 mg/ml.

21. The suspension of claim 2 comprising the hydrophobic peptide salt is suspended in the aqueous medium at a concentration of equal to or higher than 25 mg/ml.

* * * * *